United States Patent [19]

Cade et al.

[11] 4,023,560

[45] May 17, 1977

[54] FEMALE URINARY DEVICE

[76] Inventors: James Robert Cade, 529 NW. 58th St., Gainesville, Fla. 32601; James D. Raulerson, Rte. 2, Box 104, Alachua, Fla. 32615

[22] Filed: Feb. 2, 1976

[21] Appl. No.: 654,986

[52] U.S. Cl. .............................. 128/2 F; 128/295; 128/20
[51] Int. Cl.² ......................................... A61B 19/00
[58] Field of Search .......... 128/295, 294, 2 F, 127, 128/128, 3, 20; 4/110

[56] References Cited

UNITED STATES PATENTS

| | | | |
|---|---|---|---|
| 3,661,155 | 5/1972 | Lindan | 128/128 |
| 3,815,581 | 6/1974 | Levin | 128/2 F |

*Primary Examiner*—Robert W. Michell
*Assistant Examiner*—Henry S. Layton
*Attorney, Agent, or Firm*—George H. Baldwin; Arthur G. Yeager

[57] ABSTRACT

A female urinary device includes a generally inverted U-shaped, stiff and resiliently bendable, member having an upper end portion insertable into a vaginal orifice and depending spaced leg portions engaged with the vaginal wall. Spaced arm portions extend laterally forwardly from the leg portions for forcibly contacting and spreading the labia minora and majora without distorting forces being applied to the urethral orifice disposed generally between and adjacent the free ends of the arm portions. A reduced neck portion of the legs is located in the vaginal orifice after said leg portions have been squeezed together and the device is properly positioned in and on the female. The vaginal muscles engage the leg portions which correspondingly exert expanding forces within the vagina to position and stabilize the device in its operative position with the arm portions exerting expanding forces on the labia minora and majora. Outwardly directed lips are provided on the arm portions, as well as, specific shapes being provided to the arm and leg portions to effectively stabilize, position, retain and conform the device to the female urinary-genital region.

13 Claims, 12 Drawing Figures

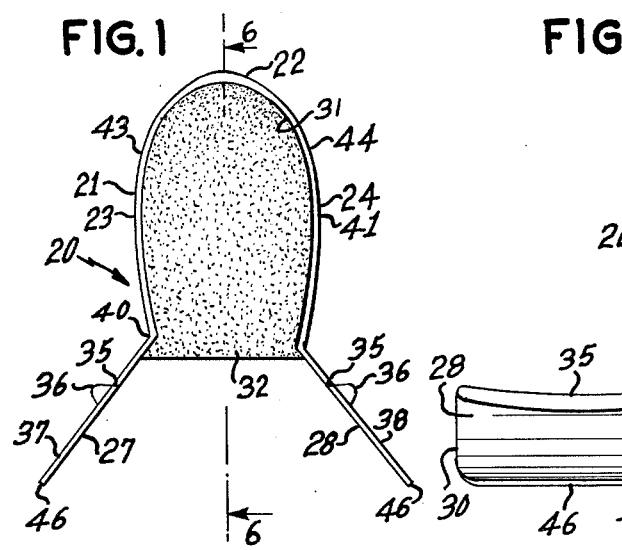
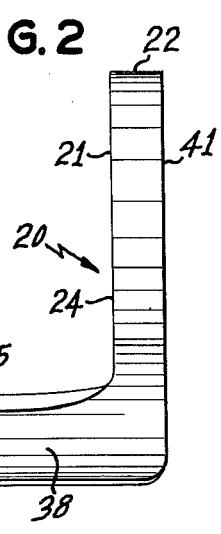
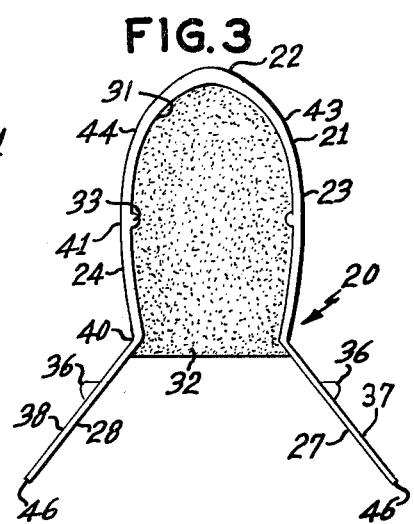
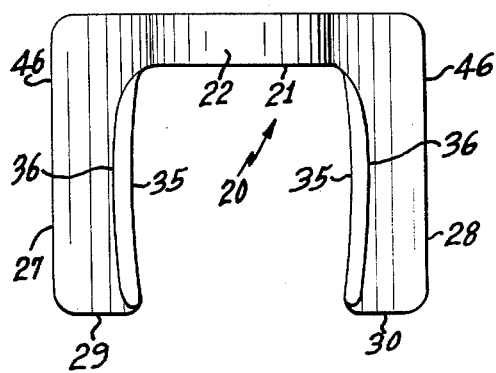
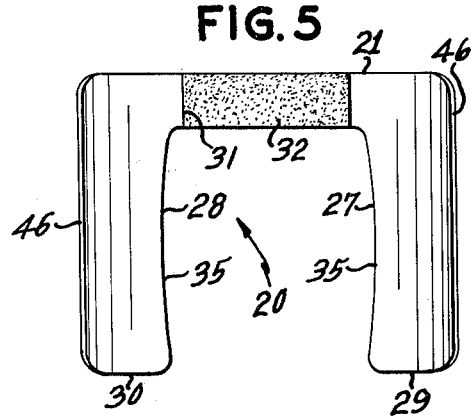
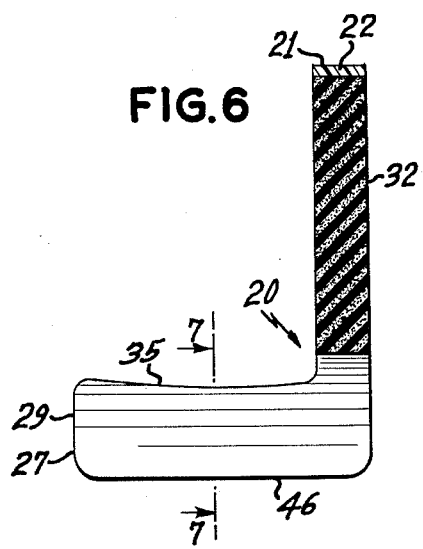
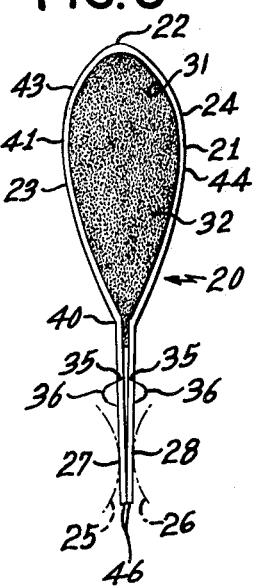

FEMALE URINARY DEVICE

BACKGROUND OF THE INVENTION

1. Field of the Invention

This invention relates to a urinary device and more particularly to a urinary device for obtaining a clean stream of urine from a female. 2. Description of the Prior Art There are many prior art devices for obtaining urine specimens from females, among which are those shown in the following U.S. Pat. Nos. 660,388; 994,884; 2,483,079; 2,490,969; 2,640,484; 2,648,335; 2,815,511; 2,840,079; 2,844,147; 2,893,678; 2,989,052 3,072,125; 3,116,734; 3,194,238; 3,335,714; 3,351,050; 3,528,423; 3,583,388; and 3,815,581; French Pat. No. 378,760 and German Pat. No. 100,854. Other patents found in the search related to vaginal speculums — U.S. Pat. Nos. 3,745,992 and 3,841,318; to a pessary —U.S. Pat. No. 982,996; and a toe spreader — U.S. Pat. No. 1,305,749. Conventional clean urine catch techniques involve manually spreading and washing of the labia majora and minora, together with other adjacent and exposed parts of the female anatomy. Then the female is urged to void the urine while the labia are so spread. These techniques usually provide poor results because the spreading of the labia is unequal thus directing the urine stream to one side or the other and washing the labia with the urinary stream, or if the spreading is too pronounced the urethral orifice is distorted from its generally round condition to an eliptical shape converting the urine stream into a fan or wide spray which washes both the right and left labia as well as the other adjacent and exposed parts of the female anatomy. There are many problems with one and other of the above prior art devices, and this invention is directed toward alleviating some of the problems with some of these devices.

BRIEF DESCRIPTION OF THE DRAWINGS

The novel features which are believed to be characteristics of this invention are set forth with particularity in the appended claims. The invention itself, however, both as to its organization and method of operation, together with further objects and advantages thereof, may best be understood by reference to the following description taken in connection with the accompanying drawings in which:

FIG. 1 is a front elevational view of the urinary device in accord with this invention;

FIG. 2 is a right side elevational view thereof;

FIG. 3 is a rear elevational view thereof;

FIG. 4 is a top plan view thereof;

FIG. 5 is a bottom view thereof;

FIG. 6 is a cross-sectional view taken along line 6—6 of FIG. 1;

FIG. 7 is a cross-sectional view taken along line 7—7 of FIG. 6;

FIG. 8 is a front elevational view similar to FIG. 1 depicting the leg members substantially squeezed together by the broken line representation of fingers;

SUMMARY OF THE INVENTION

Figure 11:
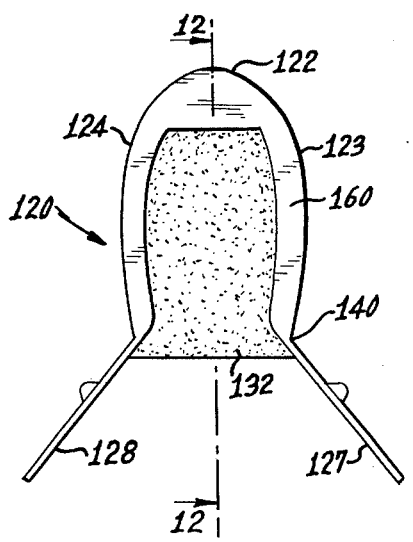
FIG. 11 is a rear elevational view of another embodiment of the urinary device in accord with this invention.

In accord with this invention a urinary device for obtaining a generally uncontaminated urine specimen from a female is seen to include a generally inverted U-shaped member having an upper end portion insertable into a vaginal orifice of a female and having depending spaced leg portions. The U-shaped member is relatively stiff, but resiliently bendable, so that the leg portions may be squeezed together for easy insertion into the vaginal orifice. The U-shaped member includes spaced arm portions extending laterally forwardly from the leg portions for forcibly contacting and spreading the labia minora and majora of a female using the device without distorting forces being applied to a female urethral orifice locatable generally between and adjacent the free ends of the arm portions. The U-shaped member is engaged by vaginal muscles and exerts expanding forces with the vagina to position and stablize the device in its operative position with the arm portions exerting expanding forces on the labia minora and majora.

Other aspects of the invention include the provision of absorbent material between the leg portions for absorbing any vaginal secretions which would tend to contaminate the stream being voided by the female. Each arm portion includes an outer surface and an elongate upper edge with an outwardly directed lip attached therealong for effectively impeding closure of the labia minora in contact with the outer surface and lip of each arm portion. The arm portions further include lower edges, the lower edges being more remotely spaced from each other than the upper edges thereby conforming the arm portions with the labia minora and majora of a female. The leg portions include outer surfaces spaced apart more closely adjacently above the arm portions so that a reduced neck portion is provided to be more conforming and anchored within a vaginal orifice of a female.

Yet other aspects relate to the integral formation of the devive from a single piece of material which is stiff to permit easy insertion of the upper end portion of the U-shaped member into a vaginal orifice and resiliently bendable by squeezing forces applied to the leg and arm portions whereby the lateral width of the device being inserted into the vagina is reduced temporarily and thereafter is permitted to resiliently expand therein for anchoring the device firmly within the vagina and forcibly holding the labia minora and majora out of the way of the urine stream being voided by a female who is using the device.

A general object of this invention is to provide an improved urinary device for obtaining a substantially uncontaminated urine specimen from a female.

A particular object is the provision of an improved urinary device which is easy to insert and position in and on a female especially by the female which expects to provide the urine specimen.

Another particular object is to provide a device with means for absorbing vaginal secretions to inhibit entrainment thereof in the urine stream being voided by the female and to effectively restrain the labia minora and majora from interference with such stream.

A specific object is the provision of an improved urinary device which is relatively confortable and conforming to the female when inserting, positioning and during voiding of the urine by the female.

Another specific object is to provide an improved urinary device which permits a relatively clean urine specimen to be obtained from a female without distorting or discomforting forces being applied to the female urethral orifice or other adjacent parts of the female urinary-genital region.

Other objects relate to a urinary device which is simple and economical in construction, simple and efficient in use, conforms in use to substantially all female adults, a serious obstacle with many prior art devices, and disposable after only a single use whereby the risk of infection to the female is minimized.

DESCRIPTION OF THE PREFERRED EMBODIMENTS

Figure 9:
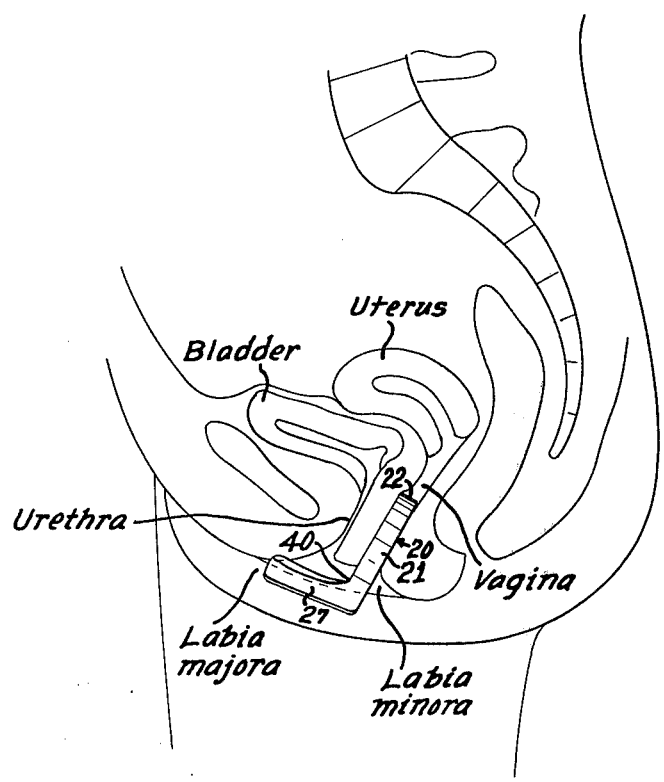
FIG. 9 is a central sectional view of a female depicting in elevation the urinary device of this invention positioned in and on a female.
Figure 10:
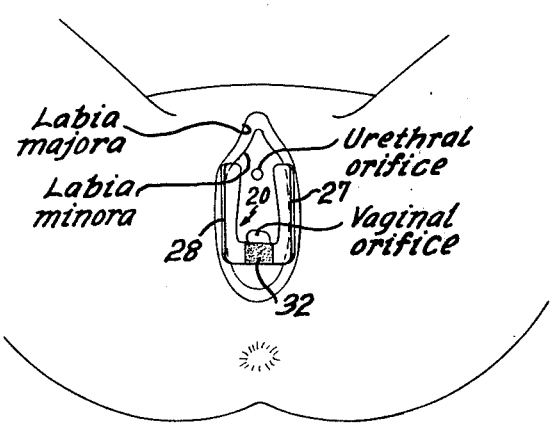
FIG. 10 is a crotch view of a female depicting a bottom view of the urinary device of this invention in and on a female.

Referring now more particularly to the drawings of FIGS. 1 to 8, a female urinary device in accord with this invention is designated by numeral 20, such device being used to obtain a generally uncontaminated urine specimen from a female, i.e., the vaginal epithelial cells, bacteria, debris and other contaminates located adjacently outwardly of the urethral orifice — such as on and surrounding the labia minora and majora — are not entrained in the urine stream when being voided after placement of device 20 in and on a female, as hereinafter more fully described in connection with FIGS. 9 and 10.

Device 20 comprises a generally inverted, stiff and resiliently bendable, U-shaped member 21 having an upper closed and rounded end portion 22 insertable in a vaginal orifice and depending spaced leg portions 23 and 24 adapted to be squeezed together, as by fingers 25 and 26 illustrated in FIG. 8, for easier insertion of the upper end portion 22 and leg portions 23 and 24 into the vagina. Upon the release of the leg portions 23 and 24, and/or laterally extending arm portions 27 and 28, the leg portions 23 and 24 exert expanding forces within the vagina to position and stablize device 20 in its operative position with the arm portions 27 and 28 extending forwardly to forcibly contact and substantially equally spread apart the labia minora and majora. Thus, the urethral orifice is exposed between the arm portions 27 and 28 adjacent the forward free ends 29 and 30 of respective arm portions 27 and 28 without distorting forces being applied to the urethral orifice.

In the cavity 31, defined by the spaced leg portions 23 and 24 and upper end portion 22, an absorbent pad 32 in the form of a fluid absorbing spongy or foraminous material, is slightly compressed so that it will not become inadvertently dislodged from cavity 31. Additionally, small molding sprues or intentionally molded nodules 33 are engaged within pad 32 to further insure that the pad 32 is not dislodged from the cavity 31, particularly during insertion, use and withdrawal of the U-shaped member 21 and pad 32 from the vagina. The utility of the general types of pads, similar to pad 32, is well known for absorbing vaginal secretions, etc., which may otherwise contaminate the urine specimen being voided by the female.

It is to be understood that construction of device 20 may be of a unitary molded plastic or the like material which is relatively stiff yet resiliently bendable whereby it may be temporarily flexed inwardly and it will continue to exert outwardly directed forces tending to regain its original condition similar to a stiff metal leaf spring. Furthermore, the arm portions 27 and 28 may be molded separately and have tabs tightly or permanently affixed within corresponding openings in the bottom parts of the leg portions 23 and 24. There are many different molding techniques and materials that could be used in constructing device 20, and it is not intended that this invention be limited to the embodiment depicted in FIGS. 1 - 8 or the other embodiment depicted in FIGS. 11 and 12.

Returning to the description of device 20, each arm portion 27 and 28 includes an elongated upper edge 35 with an outwardly directed lip 36 attached therealong, lips 36 being in contact with the labia minora to impede the closure thereof which might otherwise result if lips 36 or the like were not included in device 20. The outer surfaces 37 and 38 of arms 27 and 28 and lips 36 contact the labia minora and/or majora and cooperate to spread and maintain same out of the way of the urethral orifice and the stream being voided therefrom. A reduced neck portion 40 is provided by the leg portions 23 and 24 adjacently above the arm portions 27 and 28, portion 40 conforming more comfortably to fit within the vaginal orifice with the leg portions thereabove being nested in the vagina and the leg portions therebelow and arm portions 27 and 28 being externally of the vagina, as will be apparent from a consideration of FIGS. 9 and 10. Thus, the upper end portion 22 is reduced or tapered to present a small end for easy insertion into the vaginal orifice, followed by bulbous central portion 41 expandable to force the outer surfaces 43 and 44 against the vaginal walls and muscles, and thence the reduced neck portion 40 is effectively gripped by the vaginal muscles surrounding the vaginal orifice to firmly anchor and position the device in the vagina and to locate the arm portions 27 and 28 in appropriate positions to perform their aforementioned functions.

The arm portions 27 and 28 are seen to be generally on inclined planes relatively to the generally upright plane extending equidistantly between the leg portions 23 and 24 and arm portions 27 and 28, i.e., generally along the central axis coincident with line 6—6 of FIG. 1. These inclined planes of the arm portions 27 and 28 locate the upper edges 35 in closer spaced relation than the lower edges 46 thereby conforming the arm portions 27 and 28 to the various locations and sizes of the labia minora and majora and adjacent anatomy.

The outward forces being exerted by device 20 on the labia minora and majora adjacent the vagina are greater than the outward forces being applied thereto adjacent the outer free ends 29 and 30 of arm portions 27 and 28, since the arm portions 27 and 28 are resiliently bendable and only a part of the expanding forces exerted by the springy U-shaped member 21 is transmitted to the arm outer free ends 29 and 30. Thus the force exerted on the labia minora, for example, is not as great adjacent the uretheral orifice, and since no part of device 20 is in contact with the surrounding tissue of the uretheral orifice, the device 20 does not in anyway inhibit normal voiding of urine by the female.

Preferably the width of the leg portions 23 and 24 is about ⅝ inches with the thickness generally being about ⅛ inches except adjacent the upper end portion 22 where the thickness may be ¼ inches. The height of the arms 27 and 28 are approximately 1 inch and the length is about 1 ¼ inches. The lips 36 may extend outwardly about ¼ inch at its maximum and tapering in a flush manner adjacent the leg portions 23 and 24. The height of the device 21, as measured between a plane through lower edges 46 and the top of the upper end portion 22 is approximately 2 ¾ inches and the widths of the bulbous central portion 41 being about 1 inch and the neck portion 40 being about ¾ inches. The angle between the arm and leg portions is approximately 85° and such an acute angle has been determined to fit more different types of females than, for example, making such an angle obtuse, even though an obtuse angle may be more comfortable to some females.

Figure 12:
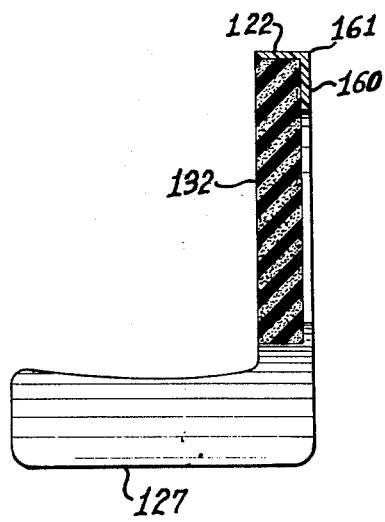
FIG. 12 is a cross-sectional view taken along line 12—12 of FIG. 11.

Another embodiment of the invention is disclosed in FIGS. 11 and 12 wherein device 120 is substantially identical to device 20, except that a U-shaped shoulder 160 extends inwardly along the rear edge 161 of the upper end portion and leg portions 123 and 124 above the neck portion 140 to further support and retain the spongy foam pad 132 therein.

In the fully operative condition, as shown in FIG. 10, and the almost fully inserted condition of FIG. 9, the device 20 is inserted first by spreading the labia majora and minora apart and introducing the upper end portion 22 into the vaginal orifice with the device being in the squeezed condition of FIG. 8 and when fully inserted the neck portion 40 is disposed generally in the vaginal orifice with the arm portions 27 and 28 released to expand outwardly to spread and retain the labia minora and majora away from the urethral orifice and out of the path of the urine stream to be voided therefrom. The spring forces of device 20 permit the insertion and retention of device in its fully operative condition without the use of a hand or strap or the like of the prior art but automatically by release of the compressive forces which temporarily bend device 20 into its squeezed condition of FIG. 8. It is to be noted that not only is device 20 useful in obtaining a voided stream of urine from a female, but also is very effective in permitting a nurse or doctor to clean the labia and urethral orifice prior to inserting a catheter into the bladder without employing one hand to spread the labia apart, clean with the other hand and then inserting the catheter with such other hand while maintaining the libia spread apart by the one hand.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to secure by Letters Patent of the United States is:

1. A urinary device for obtaining a generally uncontaminated urine specimen from a female comprising a generally U-shaped member insertable into a vaginal orifice of a female, said member including an end portion and spaced leg portions, said member further having spaced arm portions respectively extending laterally from said leg portions for forcibly contacting and spreading labia minora and majora of a female using the device without distorting forces being applied to a female urethral orifice, said member being resiliently manually bendable to bring said leg portions toward each other for ready insertion into a vaginal orifice and to bring said arm portion toward each other for ready positioning of said arm portions between labia minora and majora, said member urging said leg portion outwardly to apply expanding forces within a vagina to position and stablize said device in its operative position and urging said arm portions apart to apply expanding forces on labia minora and majora when inserted and positioned and manually released.

2. The device as defined in claim 1 further comprising absorbent material disposed between said leg portions for absorbing vaginal secretions when said leg portions are disposed within a vagina.

3. The device as defined in claim 2 further comprising means for retaining said absorbent material between said leg portions whereby inadvertent removal is inhibited.

4. The device as defined in claim 1 wherein each said arm portion includes an outer surface and an elongated upper edge, an outwardly directed lip attached along said upper edge for impeding closure of a labia minora in contact with said outer surface and lip of each said respective arm portion.

5. The device as defined in claim 1 wherein said arm portions include upper and lower edges, said upper edges of said arm portions being more closely spaced from each other than said lower edges thereby conforming said arm portions with labia minora and majora of a female.

6. The device as defined in claim 1 wherein said leg portions include outer surfaces, said outer surfaces being spaced apart more closely adjacently above said arm portions thereby forming a reduced neck portion conformable to a vaginal orifice of a female.

7. The device as defined in claim 6 wherein said leg portions bow outwardly to form a bulbous portion of said U-shaped member between said upper end portion and said neck portion.

8. The device as defined in claim 1 wherein said device is integrally formed from a single piece of material which is stiff to permit easy insertion of said member into a vaginal orifice and resiliently bendable by squeezing forces applied to said leg and arm portions.

9. The device as defined in claim 1 wherein the forces applied outwardly by said U-shaped member and arm portions is greater adjacent said leg portions than the free ends of said arm portions which are adapted to be spaced adjacent to and on either side of a uretheral orifice.

10. A urinary device for obtaining a generally uncontaminated urine specimen from a female comprising a pair of L-shaped members having a generally vertical leg and a generally horizontal arm, said legs having upper ends joined to form a smooth shape for insertion into a vaginal orifice, each leg bowing outwardly to form a bulbous central portion for engagement by vaginal walls, said leg bowing inwardly between said bulbous central portion and the lower ends thereof to form a neck portion adapted for nesting within a vaginal orifice, said arm extending forwardly from its respective said leg for engagement with and spreading of labia minora and majora of a female thereby to expose a urethral orifice between said arms without distorting forces being applied to a urethral orifice.

11. The device as defined in claim 10 wherein each said arm includes an elongated upper edge, an outwardly directed lip attached along said upper edge for effectively impeding closure of labia minora after placement of said device on a female.

12. A urinary device for obtaining a generally uncontaminated urine specimen from a female comprising a unitary member which includes a vaginal insertable portion and two arm portions, said insertable portion being resiliently bendable and generally U-shaped when relaxed with generally parallel side legs extending from a curved leading end joining said legs, each side leg being joined to a respective arm portion remote from said leading end, said member being resiliently manually bendable from said relaxed shape to bring said legs toward each other for ready insertion of said insertable portion into a vaginal orifice and to bring said arm portion toward each other, said insertable portion resiliently urging said arm portions apart and into contact with and spreading apart labia minora and majora when inserted and manually released.

13. The device in accord with claim 12 wherein said arm portions have free ends spaced apart and locatable generally on opposite sides of a female urethral orifice when inserted and manually released.

* * * * *